(12) United States Patent
Chao et al.

(10) Patent No.: US 9,927,364 B1
(45) Date of Patent: Mar. 27, 2018

(54) LINE-SCAN RAMAN IMAGING METHOD AND APPARATUS FOR SAMPLE EVALUATION

(71) Applicants: Kuanglin Chao, Ellicott, MD (US); Moon S. Kim, Silver Spring, MD (US); Jianwei Qin, Ellicott City, MD (US)

(72) Inventors: Kuanglin Chao, Ellicott, MD (US); Moon S. Kim, Silver Spring, MD (US); Jianwei Qin, Ellicott City, MD (US)

(73) Assignees: The United States of America, as represented by The Secretary of Agriculture, Washington, DC (US); University of Maryland, College Park, MD (US)

( * ) Notice: Subject to any disclaimer, the term of this patent is extended or adjusted under 35 U.S.C. 154(b) by 342 days.

(21) Appl. No.: 14/069,827

(22) Filed: Nov. 1, 2013

(51) Int. Cl.
*G01N 21/65* (2006.01)

(52) U.S. Cl.
CPC .................................. *G01N 21/65* (2013.01)

(58) Field of Classification Search
CPC .. G01J 3/28; G01J 3/2823; G01J 3/44; G01N 21/65; G02B 26/10
See application file for complete search history.

(56) References Cited

U.S. PATENT DOCUMENTS

| | | | | |
|---|---|---|---|---|
| 5,309,255 A * | 5/1994 | Brandt | ................... | G02B 26/10 250/585 |
| 6,128,077 A * | 10/2000 | Jovin et al. | ................... | 356/310 |
| 6,466,045 B1 * | 10/2002 | Tran | ......................... | 324/756.02 |
| 6,646,264 B1 * | 11/2003 | Modiano et al. | ......... | 250/339.07 |
| 2006/0019409 A1 * | 1/2006 | Nelson et al. | ................ | 436/524 |
| 2007/0216898 A1 * | 9/2007 | Gardner, Jr. | .............. | G01J 3/02 356/301 |
| 2009/0066934 A1 * | 3/2009 | Gao | ................... | G01N 15/1463 356/73 |
| 2011/0261354 A1 * | 10/2011 | Sinfield | ..................... | G01J 3/02 356/301 |
| 2012/0257196 A1 * | 10/2012 | Raicu et al. | .................. | 356/300 |
| 2014/0197335 A1 * | 7/2014 | Jayasooriya | ........... | G01N 21/65 250/459.1 |

OTHER PUBLICATIONS

Qin et al. "Raman Chemical Imaging System for Food Safety and Quality Inspection", vol. 53(6): 1873-1882 Transactions of the ASABE, American Society of Agricultural and Biological Engineers, 2010.*
Qin et al. "Nondestructive evaluation of internal maturity of tomatoes using spatially offset Raman spectroscopy" Postharvest Biology and Technology 71 (2012) 21-31.*

* cited by examiner

*Primary Examiner* — Dominic J Bologna
(74) *Attorney, Agent, or Firm* — John D. Fado; Robert D. Jones (57) ABSTRACT

A line-scan laser is directed to a sample so that a Raman-shifted light signal is emitted from the sample. An imaging spectrograph and associated camera and processor acquires the Raman-shifted light signal and processes the signal to thereby identify the composition of the sample.

37 Claims, 13 Drawing Sheets

LINE-SCAN RAMAN IMAGING METHOD AND APPARATUS FOR SAMPLE EVALUATION

FIELD OF THE INVENTION

The disclosed method and apparatus relates to the evaluation of relatively large samples of particulate materials. Specifically, the system and method described herein relates to a line-scan Raman imaging method and apparatus for evaluating relatively large (dry) powdered samples.

BACKGROUND OF THE INVENTION

A wide variety of particulate-type food materials are available for purchase in commercial outlets. These foods include meals, powders, and granulated products that may be mixed with a liquid to produce common food substances. Detecting and preventing contamination of these substances is an important challenge facing the food industry.

For example, melamine, a common industrial chemical, has been intentionally mixed with food substances as a way to boost products' apparent protein content. Significantly, melamine has been found in powdered milk and milk substitutes intended for infant consumption. Melamine was also used as a binder when making pellet feed for animals. Consequently melamine-contaminated food is a major safety concern.

In addition to melamine, small amounts of cyanuric acid, ammeline, and ammelide were also detected in pet feed and in the tissue and urine of dead pets that consumed the contaminated food. Although it may be possible that cyanuric acid, ammeline, and ammelide were added as contaminants, it is more likely that their presence in pet food resulted from the degraded derivatives of melamine.

Prior art methods of detecting contamination in particulate food substances are effective, but may be relatively slow, and the tested food samples are relatively small in comparison to the speed and the size of samples that can be tested using the method and apparatus described herein. U.S. Pat. No. 8,467,052 to Chao uses a point-source laser to test particulate materials for contaminates. Although the Chao method is effective, it is not nearly as fast as the method described herein.

The need exists for a method and apparatus to more quickly test larger sample volumes of particulate-based materials. The current invention describes a method that reduces test times from hours to minutes, and significantly increases the size of samples to be tested. The current method and apparatus achieves these improvements while meeting or exceeding the accuracy and consistency of the prior art processes.

SUMMARY OF THE INVENTION

This disclosure is directed to a method for determining a composition of a sample. In accordance with the method, a laser-emitting device emits a line-scan laser beam. The line-scan laser beam is directed to a beamsplitter which deflects the line-scan laser beam onto a sample. The line-scan laser beam traverses the sample thereby causing the sample to emit a Raman light signal. A spectrograph receives the light signal and disperses the light signal to generate spectral data. A camera connected to the spectrograph receives the spectral data and forms a spectrum for each pixel of a line-scan image. The spectrum for the line-scan image is transmitted to a computer processor so that the processor receives the spectrum for each pixel of the line-scan image and determines a composition of the sample.

This disclosure is also directed to an apparatus for determining a composition of a sample. The apparatus includes a laser-emitting device that emits a line-scan laser beam. A beam splitter deflects the line-scan laser beam so that the line-scan laser beam traverses a sample disposed in a sample retention reservoir. As the line-scan laser beam traverses the sample, the sample emits a Raman light. A spectrograph receives the light signal, and disperses the light signal to generate spectral data. A camera receives the spectral data and forms a spectrum for each pixel of a line-scan image. A processor receives the spectrum for each pixel of the line-scan image and determines a composition of the sample.

The disclosure is further directed to a system for determining a composition of a sample. The system includes a beamsplitter structured to deflect a line-scan laser beam onto a sample so that a Raman light signal is generated. The system also includes a spectrograph structured so that a spectrograph input slit is aligned in a same vertical plane an excitation line defined by the line-scan laser beam. The system further includes a processor that is in communication with the spectrograph so that the processor determines a composition of the sample based on the Raman light signal.

The disclosure is additionally directed to a further method for determining a composition of a sample. A beamsplitter deflects a line-scan laser beam onto a sample so that the sample emits a Raman light signal. A spectrograph is positioned so that an input slit in the spectrograph is aligned in a same vertical plane as an excitation line defined by the line-scan laser. The Raman light signal is detected by the spectrograph through the input slit and Raman light signal data is communicated from the spectrograph to a processor so that the processor determines a composition of the sample based on the Raman light signal data.

DETAILED DESCRIPTION OF PREFERRED EMBODIMENTS

Figure 1:
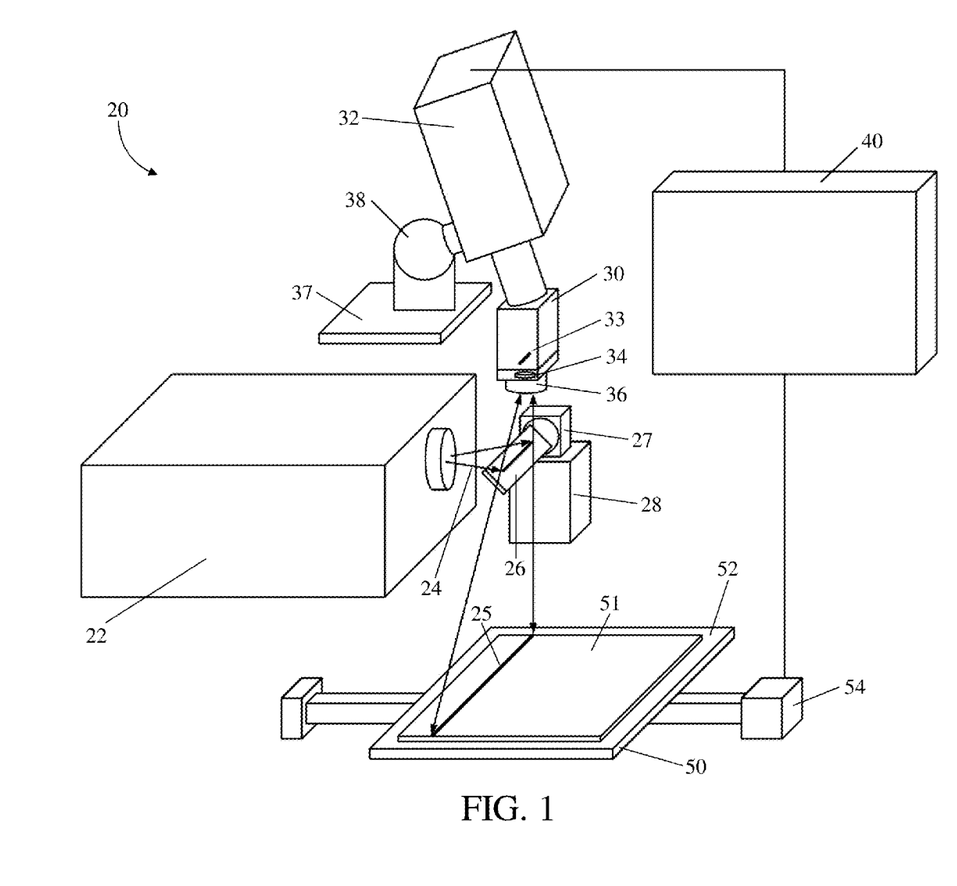
FIG. 1 is a schematic view of the apparatus described herein.
Figure 2:
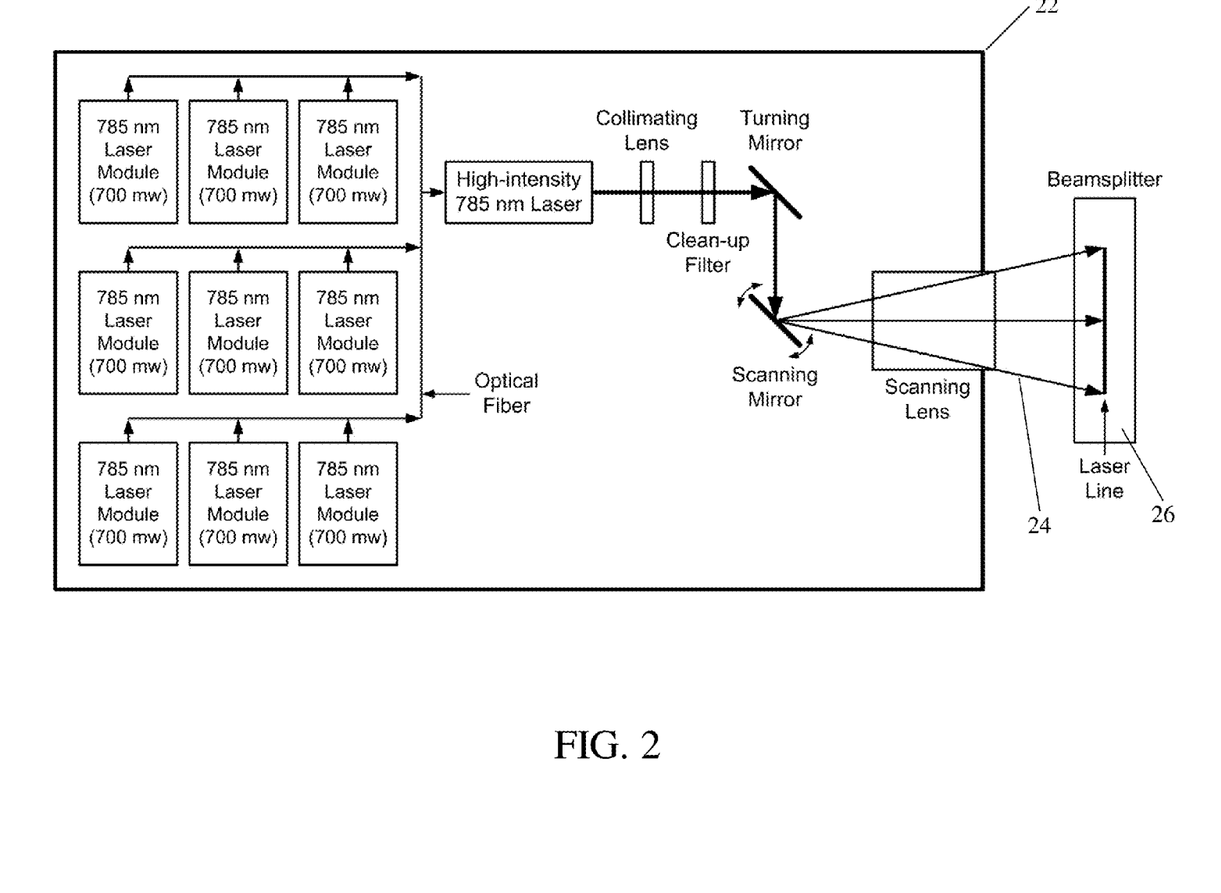
FIG. 2 is schematic of the laser-emitting device (including the beamsplitter).

As generally shown in FIG. 1, the apparatus described herein comprises a line-scan Raman chemical imaging system 20. A custom-designed high-power 785 nm line laser-emitting device 22 (Innovative Photonic Solutions, Monmouth Junction, N.J., USA) is used as the Raman excitation source. A schematic of the laser-emitting device 22 is shown in FIG. 2. Note that the portion of the laser-emitting device 22 inside the rectangle on the left side of FIG. 2 is prior art commercial product.

The laser-emitting device 22 described herein has an advantage over short-wavelength lasers for reducing fluorescence emissions from targeted samples. As best shown in FIG. 2, the laser-emitting device 22 comprises nine 700 mW spectrum-stabilized laser modules that are mounted on the bottom of the unit 22. Laser light generated from the nine modules is collected by nine separate optical fibers and converged together to form a high-intensity laser beam. The converged light passes through a collimating lens and 785 nm laser clean-up filter for the purpose of beam collimation and elimination of amplified spontaneous emission noise. As shown in FIG. 2, a turning mirror then changes the light propagation direction by 90° and guides the laser beam to reach a scanning mirror. The scanning mirror oscillates at a scan rate of 250 Hz (4 ms per full cycle sweep) so that the laser point is spread at the oscillating mirror surface to form a line-scan laser 24.

As shown in FIGS. 1 and 2, the line-scan laser beam 24 is projected onto a 785 nm dichroic beamsplitter 26 (LPD01-785RS, Semrock, Rochester, N.Y., USA) after passing through a scanning lens of the laser-emitting device 22. The beamsplitter 26 is fixed on a rotation stage 27 that is mounted on a XYZ translation stage 28. Both stages are manually controlled to provide flexible positioning for the beamsplitter 26. In the preferred embodiment, the beamsplitter 26 is 10 cm long, and it reflects the 785 nm line-scan laser beam 24 (~6 cm on the beamsplitter surface) incident at 45° to create a 24 cm long "excitation laser line" 25 at a vertical distance of ~30 cm.

In alternative embodiments, the line-scan laser 25 may comprise laser beams having wavelengths longer or shorter than 785 nm. For example, lasers in the 500 nm or 1000 nm range may be practical for the system described herein.

For the purposes of this disclosure, the (generally linear) area illuminated by a sweep of the line-scan laser beam comprises the "excitation laser line" 25. A portion of the excitation laser line 25 may be visible to the human eye and appears as an essentially solid laser line on a surface of the sample 51.

A Raman imaging spectrograph 30 (ImSpector R10E, Specim, Oulu, Finland) is mounted to a camera 32. The spectrograph 30 is built using a prism-grating-prism (PGP) component. The input slit 33 is 14.2 mm long and 30 μm wide, and detects and admits the Raman light signals emitted from a sample when the sample is illuminated by the line-scan laser. After entering the spectrograph, the Raman light signal is dispersed into different wavelengths after passing through the spectrograph PGP component assembly. The dispersed light is then projected onto an area detector, creating a 2-D spatial-spectral image: one dimension represents spatial and the other spectral.

In the preferred embodiment, the imaging spectrograph 30 covers a wavelength range of 770-980 nm (or a Raman shift range of −248.2-2534.8 $cm^{-1}$) with a spectral resolution of 0.3 nm (~10 $cm^{-1}$). A 785 nm long-pass filter 34 (BLP01-785R-25, Semrock, Rochester, N.Y., USA) is fixed in the filter holder inside the front C-mount of the spectrograph 30 to block the light at and below the laser wavelength of 785 nm (i.e., Rayleigh and anti-Stokes scattering). A manual iris C-mount lens 36 (Xenoplan, Schneider Optics, Van Nuys, Calif., USA) is attached to the imaging spectrograph 30 for aperture and focus adjustment.

In the preferred embodiment, a 16-bit high-performance charged coupled device (CCD) camera 32 (iKon-M 934, DU934P-BR-DD, Andor Technology Inc., South Windsor, Conn., USA) is used to collect the Raman image data. The camera 32 has an area array of 1024×1024 pixels on a 13.3×13.3 $mm^2$ sensor area, with quantum efficiency (QE) greater than 90% at 800 nm and about 45% at 1000 nm. The camera 32 is thermoelectrically cooled to −65° C. during spectral image acquisition to minimize the dark current.

The camera 32 is fixed on a ball and socket mounting stage 38 that is mounted on top of a manual translation stage 37. The two stages 37, 38 provide spherical and horizontal motion for placing the camera 32 and the imaging spectrograph 30 at the optimal position to collect the Raman light signals. The camera 32 is connected to a computer processor 40 using a USB cable, through which both camera control and data transfer are carried out.

A programmable, one-axis motorized positioning table 50 (XN10-0180-E25-21, Velmex, Bloomfield, N.Y., USA) is used to move the sample 51 (deposited in a sample retention area 52 on a top portion of the table 50) relative to the excitation laser line 25. The movement of the table 50 is controlled by the computer via a stepping motor controller 54. In the preferred embodiment, the table 50 has a square sample retention area 52 of 30×30 $cm^2$, and it can travel in a distance of 45 cm with a displacement resolution (advance per step) of 1.5875 μm.

For the sake of clarity, some conventional mounting and positioning hardware is not shown in FIG. 1. In the preferred embodiment, the positioning table 50 is mounted on a base optical breadboard. Two other breadboards along with solid stainless steel posts are used to mount the laser-emitting device 22 and the ball and socket mounting stage 38, respectively. The whole imaging system 20 is housed within an aluminum-framed enclosure with black foam boards to avoid the influence of ambient light.

System Software

Figure 3:
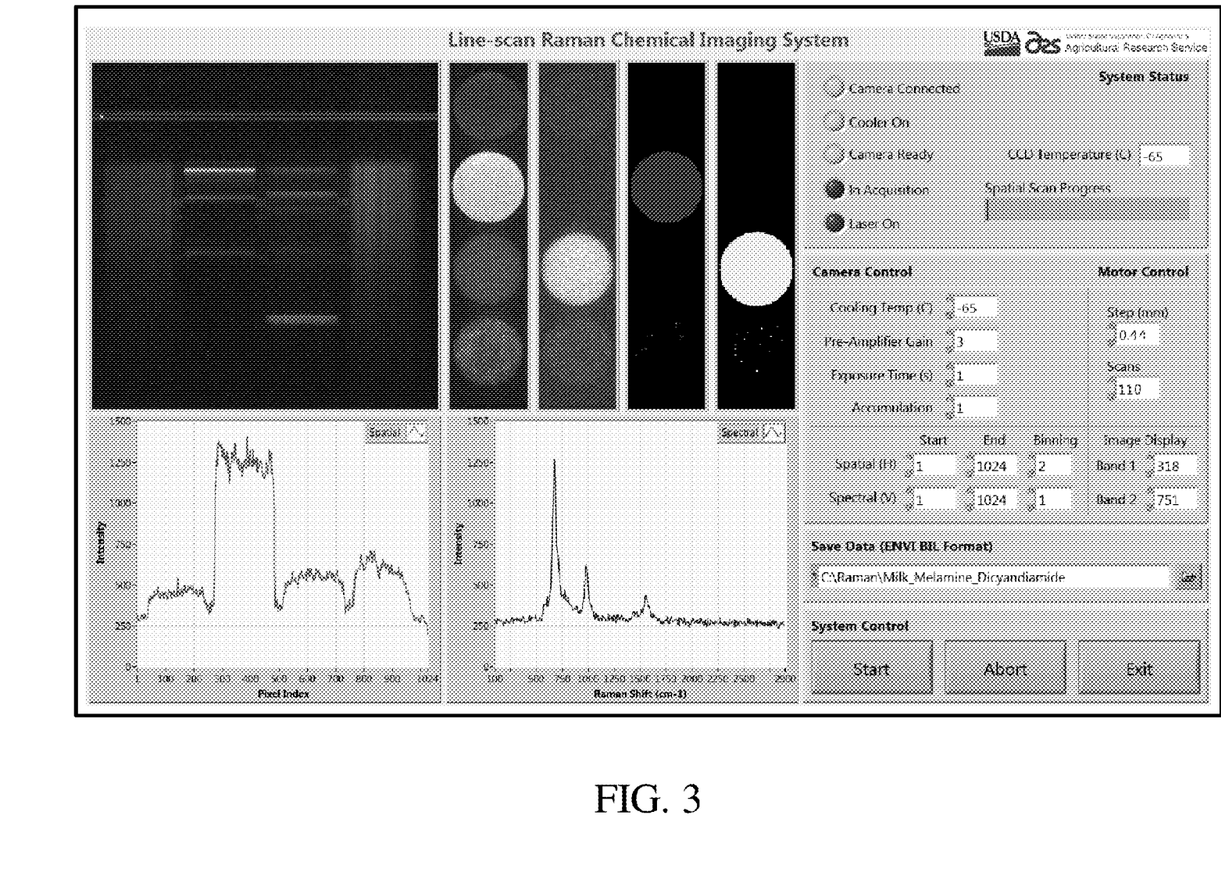
FIG. 3 is color representation of a user-to-software.

A preferred embodiment of the user-software interface is shown in FIG. 3. The system software for the system 20 was developed using LabVIEW with Vision Development Module (National Instruments, Austin, Tex., USA) in the Microsoft Windows operating system. The parameterization and data-transfer functions (e.g., camera control, image acquisition, sample movement, and synchronization) were fulfilled in the LabVIEW programming environment using Software Development Kits (SDKs) provided by the manufacturers of the camera 32 and the stepping motor controller 54. An original 2-D spatial-spectral image from the camera 32 is shown and updated for each scan. A spatial profile and a spectrum extracted at the mouse cursor position in the image are plotted to let users monitor the Raman scattering signals in both spatial and spectral domains.

Raman images of the samples at user-selected bands are displayed and accumulated line by line to show the scan progress in real time. The 3-D hyperspectral Raman image data are saved in the format of Band Interleaved by Line (BIL), which can be analyzed by commercial software packages such as ENVI (ITT Visual Information Solutions, Boulder, Colo., USA). Real-time image processing functions are incorporated in the software to generate chemical images for visualizing quantity and spatial distribution of interested targets for particular food safety and quality applications.

System Operation

The line-scan Raman system 20 acquires hyperspectral image data using a "pushbroom" method. Specifically, a virtual data hypercube is constructed as the positioning table 50 moves the sample 51 in a linear and methodical manner through area scanned by the line-scan laser beam 24 so that the entire sample 51 is eventually scanned.

The maximum output power of the line-scan laser beam 24 is approximately 5 W. The laser intensity can be adjusted by dialing the laser drive current as read out on an LED digital panel meter of the laser-emitting device 22. A focus knob on the back panel of the laser-emitting device 22 can be used to sharpen the laser line to less than 1 mm wide.

Figure 4:
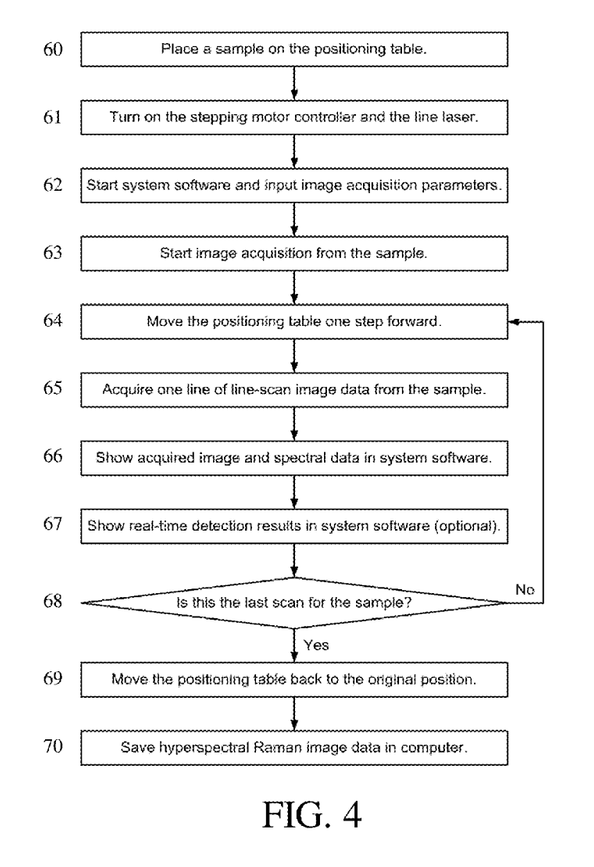
FIG. 4 is a flowchart showing the automated chronological process of scanning a sample for potential contamination.

FIG. 4 comprises a flow chart that describes the automated chronological process of scanning a sample for potential contamination. FIG. 4 also describes the process for providing information for the software-user interface shown in FIG. 3. Specifically, FIG. 4 steps 64-68 show how the data for the virtual data hypercube is obtained as (per FIG. 1) the positioning table 50 moves the sample 51 in a linear and methodical manner through area scanned by the line-scan laser beam 24 until the entire sample 51 has been scanned.

Figure 5:
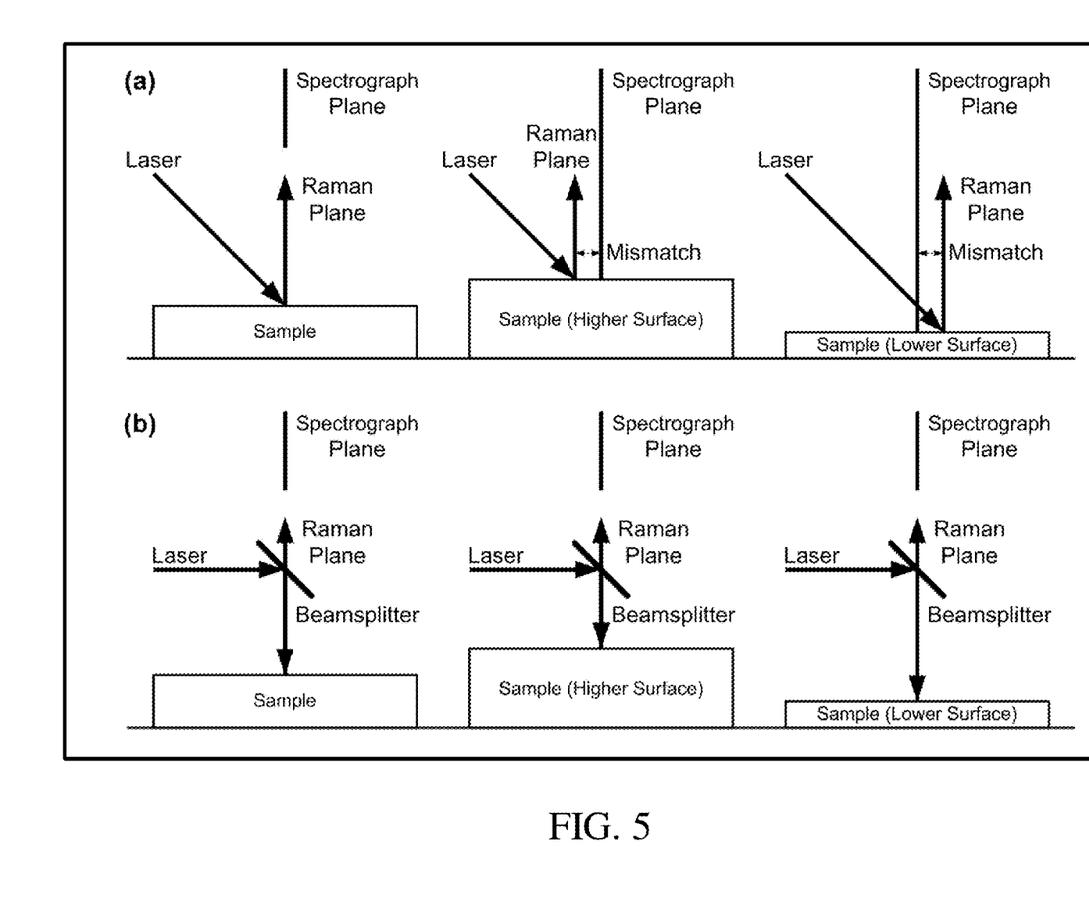
FIG. 5 shows the effect of laser incident angle on line-scan Raman image acquisition: (a) oblique and (b) normal incidence on the sample surface with different sample profiles. The configuration shown in section (b) comprises the preferred embodiment described herein.

As best shown in FIG. 5, the angle of incidence of the line-scan laser beam is critical for efficiently acquiring the Raman light signals. Oblique incidence of the line-scan laser beam will make the system sensitive to the height of the samples. As shown in FIG. 5 section (a), a sample with a higher or lower surface profile will change the location of the vertical plane (labeled "Raman Plane" in FIG. 5) where the line-scan laser illuminates the surface of the sample. Consequently the spectrograph input slit vertical plane (labeled "Spectrograph Plane" in FIG. 5) may not align with the Raman Plane. Raman light signals are emitted (in the Raman Plane) from the sample when the line-scan laser beam illuminates the surface of the sample. If the Raman Plane is not aligned with the Spectrograph Plane then the quality of the Raman light signal (and the associated data) is substantially degraded.

Essentially, for the purposes of this disclosure, the term "Raman Plane" describes a vertical plane passing through (and defined by) the excitation laser line, i.e. a line in a sample illuminated in one sweep of a line-scan laser beam. The term "Spectrograph Plane" describes a vertical plane passing through (and defined by) the input slit of an imaging spectrograph comprising a PGP.

Alternatively to the configuration shown in FIG. 5 section (a), in FIG. 5 section (b) (i.e. the preferred embodiment), the system is not affected by varying the height of the sample. In accordance with the preferred embodiment, the beamsplitter is angled at about 45° so that the line-scan laser beam has an angle of incidence of about 45° relative to the face of the beamsplitter. Consequently the Raman Plane is consistent and essentially vertical, and normal to the surface of the sample, so that the height of the sample does not affect the alignment of the Raman Plane with the Spectrograph Plane. Further, the consistency of the location of the Raman Plane enables alignment between the Raman Plane and the Spectrograph Plane, thereby significantly improving the quality of the Raman light signal detected by the imaging spectrograph as well as the spectral data eventually derived from the Raman light signal.

In operation, the dichoric beamsplitter deflects the line-scan laser line so that the trajectory of the line-scan laser beam is essentially normal to the surface of the sample. As the sample is illuminated by the line-scan laser beam, the sample emits a Raman-shifted light signal The beamsplitter allows Raman-shifted light signals having longer wavelengths to pass back through the beamsplitter unaltered so that the light signals are detected by an imaging spectrograph through the spectrograph input slit.

Spectral Calibration Example

Spectral calibration for Raman spectroscopy and imaging systems aims to define the relative Raman shift positions (i.e., wavenumbers) along the spectral dimension rather than the absolute wavelengths. In general, chemical standards with known relative wavenumber shifts excited by a source with a fixed wavelength are used instead of the spectrally established light sources used for absolute wavelength calibrations.

In this disclosure, two Raman shift standards, polystyrene and naphthalene, were used for spectral calibration of the line-scan Raman imaging system. Each chemical was placed in an individual Petri dish (47 mm in diameter), and they were scanned by the Raman imaging system. The spectral calibration results are summarized in FIGS. 6-8.

Figure 6:
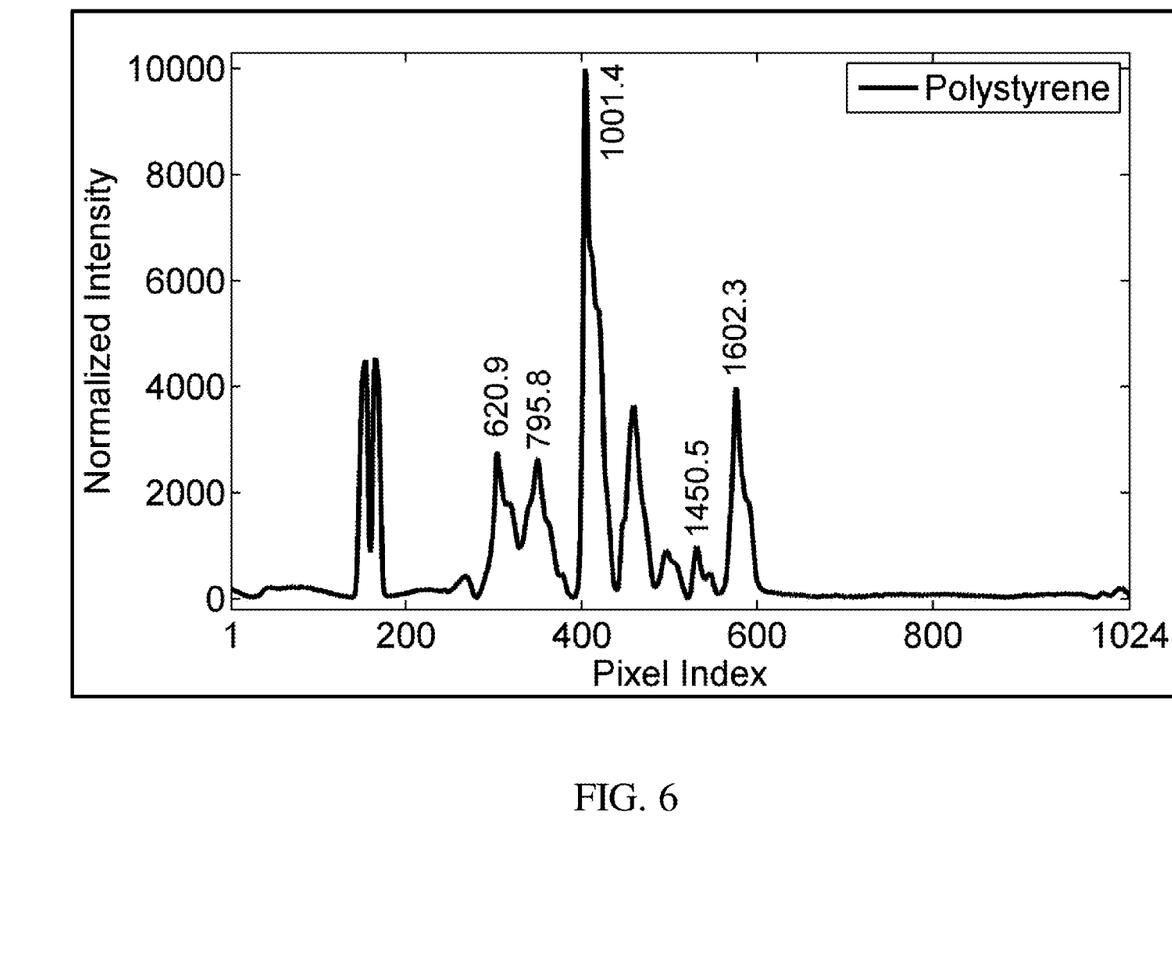
FIG. 6 is a Raman spectrum for polystyrene.
Figure 7:
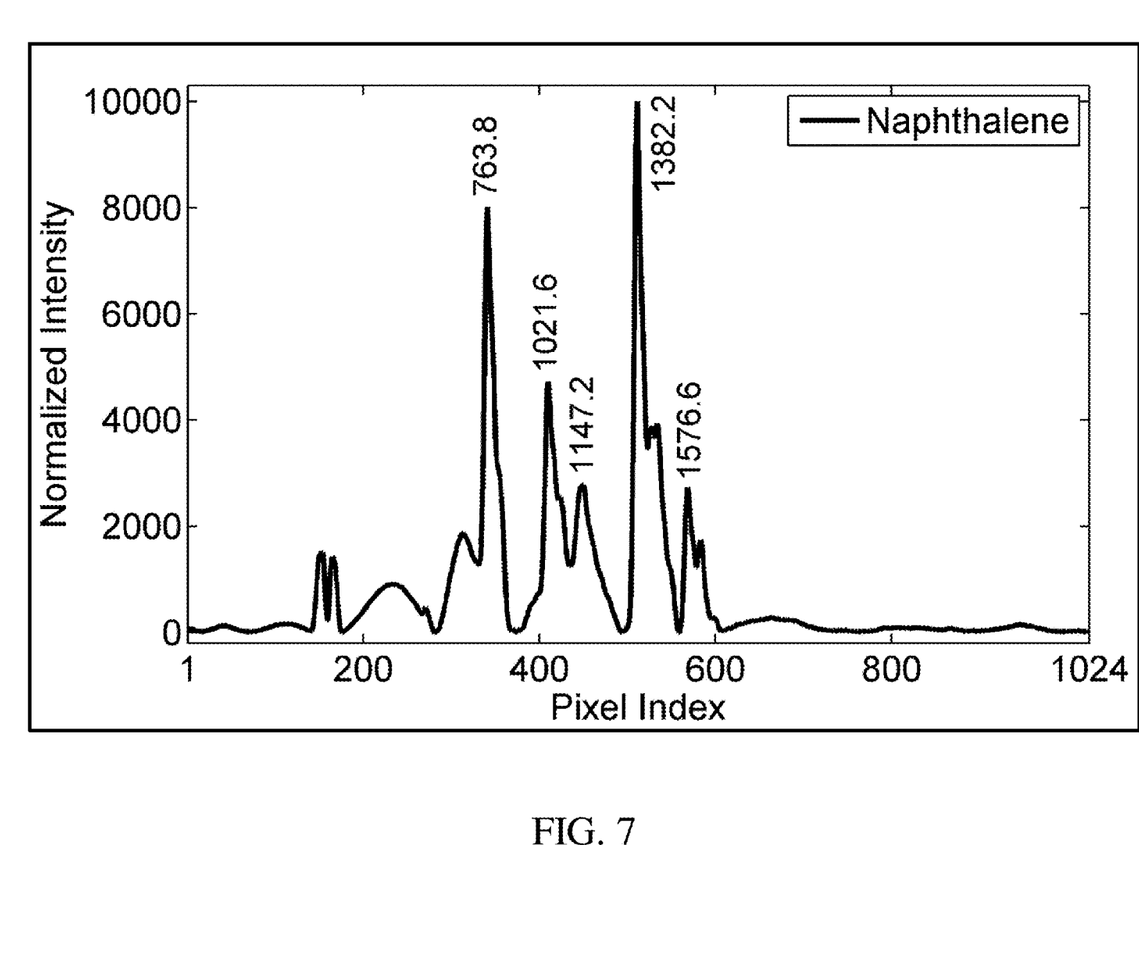
FIG. 7 is a Raman spectrum for naphthalene.
Figure 8:
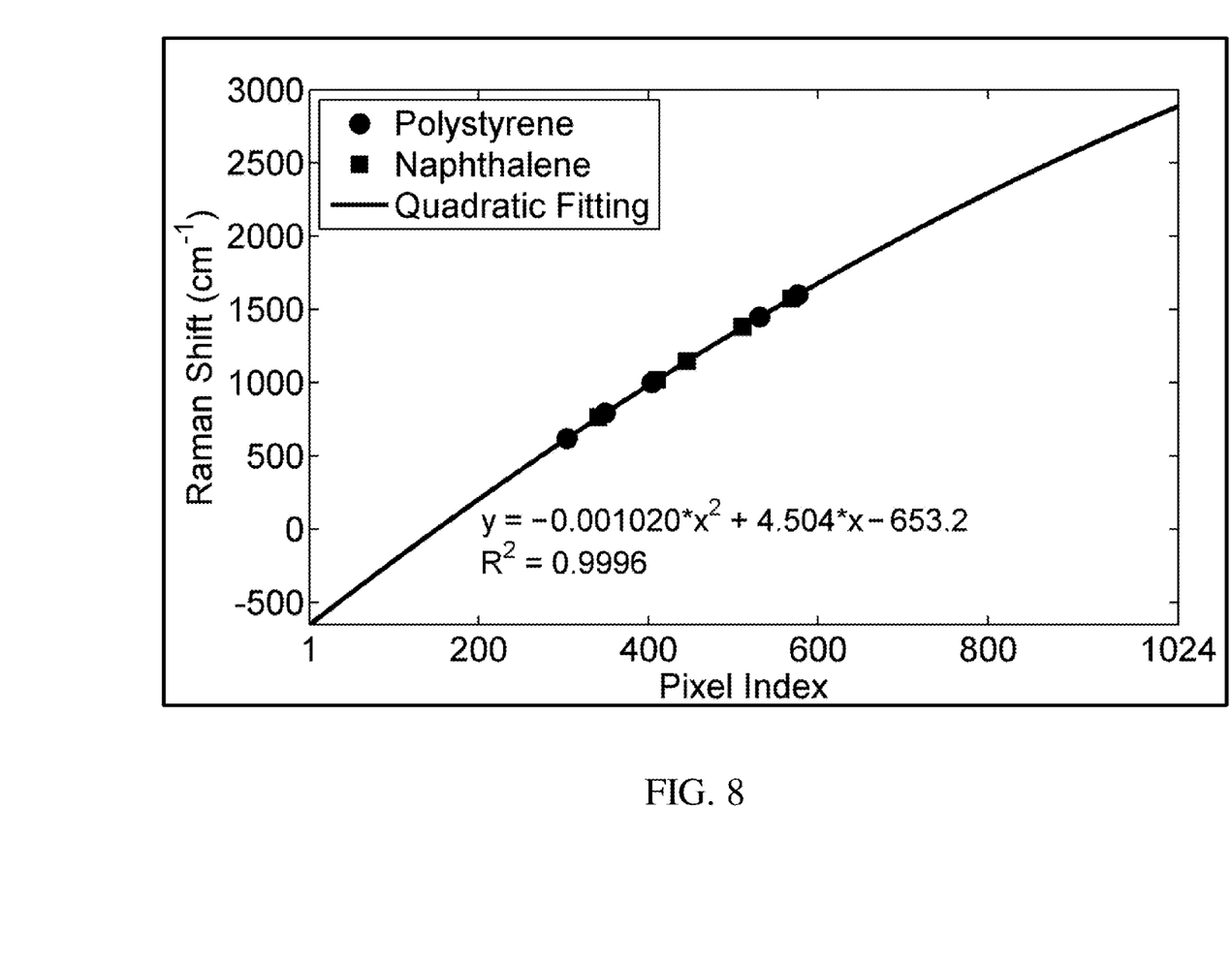
FIG. 8 is a plot showing a quadratic regression fitting for polystyrene and naphthalene.

Representative Raman spectra of polystyrene and naphthalene are shown in FIGS. 6 and 7, respectively. The two spectra are the results after fluorescence baseline correction and normalization, and each plot is an average of 25 spectra extracted from an image area of 5×5 pixels. For each sample, five Raman peaks were selected for establishing the relationship between the ten known wavenumbers (marked in FIGS. 6 and 7) and the corresponding pixel indices.

Figure 9:
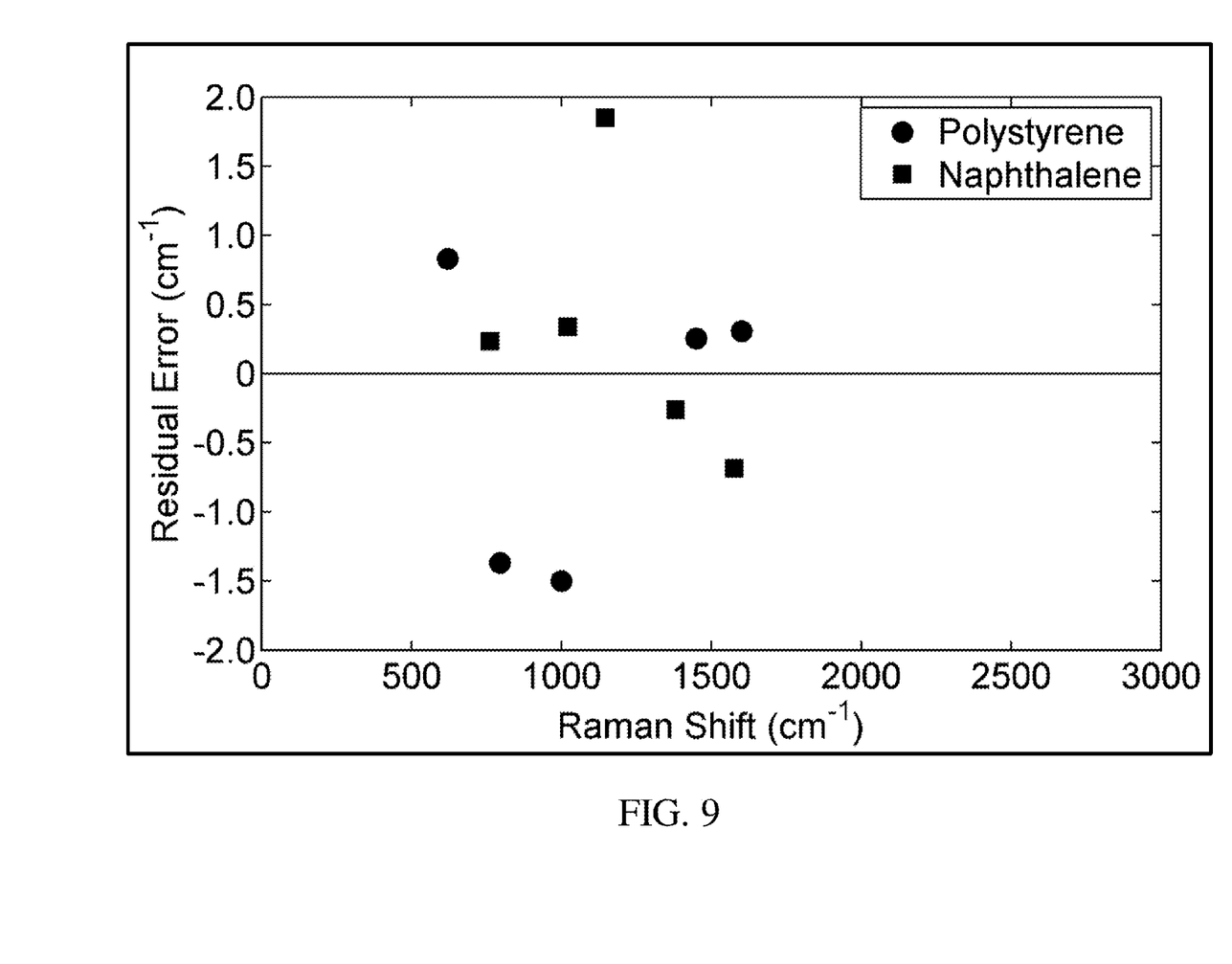
FIG. 9 is a plot showing residual errors for the regression model for polystyrene and naphthalene.

A quadratic function was used for regression analysis (FIG. 8), and the model resulted in an $R^2$ of 0.9996. The residual errors of the quadratic fitting are shown in FIG. 9. The error values at the ten selected wavenumbers are less than 2 $cm^{-1}$, demonstrating the effectiveness of the quadratic function for fitting the data. Based on the quadratic model, the Raman shift range covered by the imaging system can be calculated as −648.7 to 2889.0 $cm^{-1}$ with a wavenumber interval less than 4.5 $cm^{-1}$.

Spatial Calibration Example

The spatial resolution along the sample moving direction depends on the step size of the movement. The resolution for the spatial axis parallel to the excitation line is determined by combined factors involving working distance, lens, imaging spectrograph, and camera. Given a fixed number of pixels, the spatial resolution and the length of the instantaneous field of view (IFOV) are a pair of trade-off parameters. They can be adjusted by changing the lens-to-sample distance and the focal length of the lens to accommodate different imaging applications.

Under a setup of using a lens with 23 mm focal length and a working distance of 370 mm, the length of the IFOV of the imaging system was determined as 230 mm. The spatial resolution in the transverse direction thus can be calculated as 230 mm/1024 pixels=0.22 mm/pixel. The length of the IFOV was reduced to 72 mm when a 35 mm lens and a 200 mm working distance were used. The spatial resolution was increased as 72 mm/1024 pixels=0.07 mm/pixel. Such flexibility for acquiring spatial information enables the imaging system described herein to inspect food items with different sizes.

Figure 10:
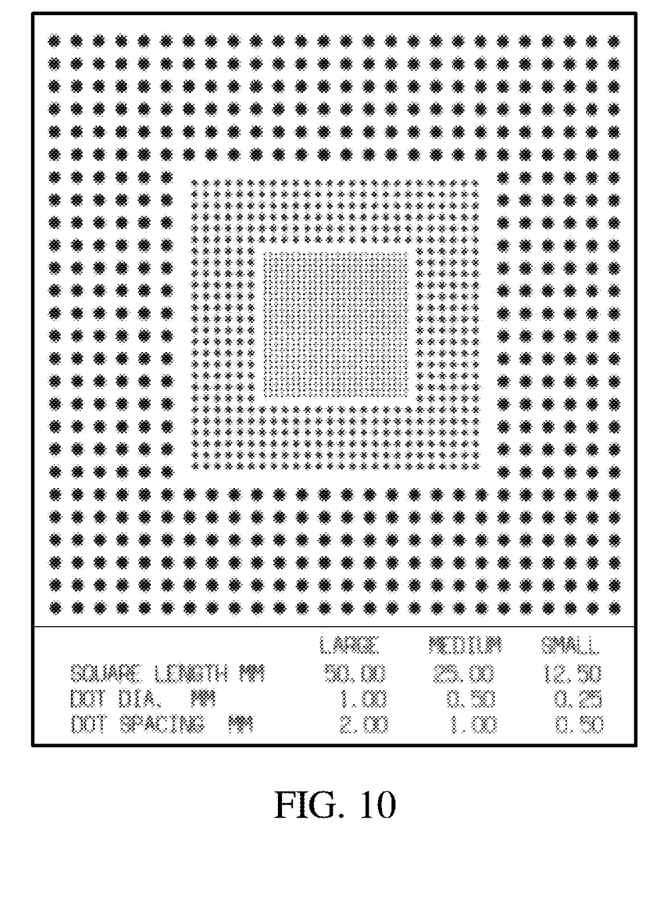
FIG. 10 is a resolution test chart imaged by the line-scan Raman imaging system with a step size of 0.07 mm.

A single-band image obtained from a standard resolution test chart using the second setup mentioned above is shown in FIG. 10. The line-scan laser was used to illuminate the glass chart placed on a piece of white paper. A step size of 0.07 mm was used to scan the chart to provide a near-square pixel size of 0.07×0.07 mm. The diameter of the smallest dots in the central chart area is 0.25 mm, and the distance between these dots is 0.5 mm. The outermost large dots (1 mm in diameter) are printed within a 50 mm square. No distortions were observed from the dots in the image, and the 0.25 mm dots can be resolved owing to the high spatial resolution for both scanning and transverse directions.

Milk Powder Authentication Example

The performance of the line-scan Raman imaging system described herein is demonstrated by an example application directed to the authentication of milk powder. Two chemical adulterants, melamine and dicyandiamide (St. Louis, Mo., USA), were mixed into skim milk powder (Organic Valley, La Farge, Wis., USA) to create a mixed sample with a concentration of 2.0% (w/w) for each adulterant.

A vortex mixer was used to shake and spin a centrifuge tube containing the mixture to ensure even distribution of the adulterant particles in the milk powder. Besides the mixed sample, pure milk powder, pure melamine and pure dicyandiamide were also prepared for the purpose of comparison. The four powder samples were put in four Petri dishes, each petri dish having a diameter of 47 mm.

The Raman imaging system (described herein) equipped with a 23 mm focal length lens scanned the samples in the four Petri dishes, aligned in a row, using a camera exposure time of 1.0 s, a camera spatial binning of 2, and a step size of 0.44 mm, resulting in a 512×110×1024 hypercube (1024 bands). Under these settings, it took approximately four minutes to finish the scan for the row of four samples. A dark current image was collected with the line-scan laser off and a cap covering the 23 mm camera lens. This dark current image was subtracted from the image of the four samples before any further analysis of the image, to account for any noise produced by low level current in the camera imaging detector.

Figure 11:
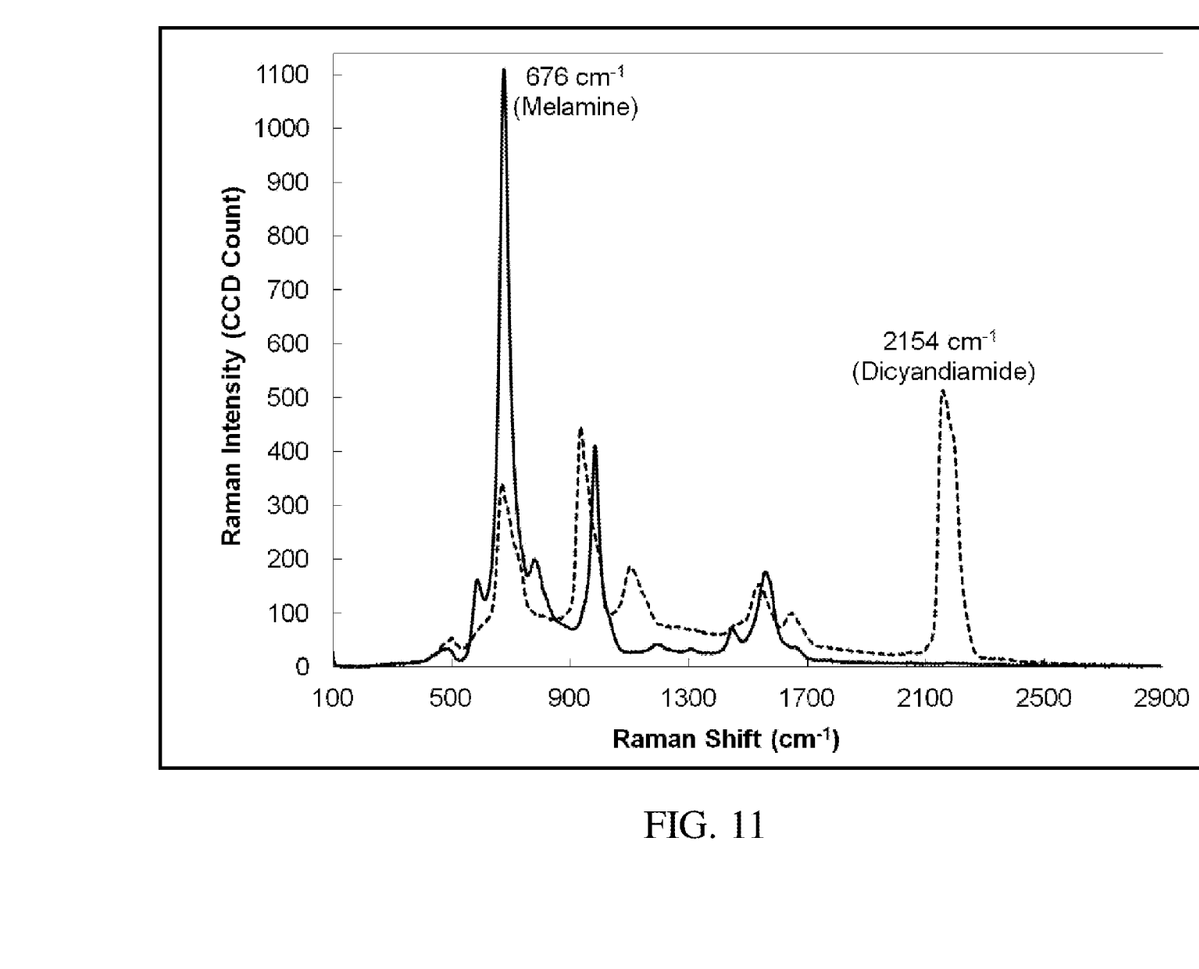
FIG. 11 is Raman spectra of melamine and dicyandiamide.
Figure 12:
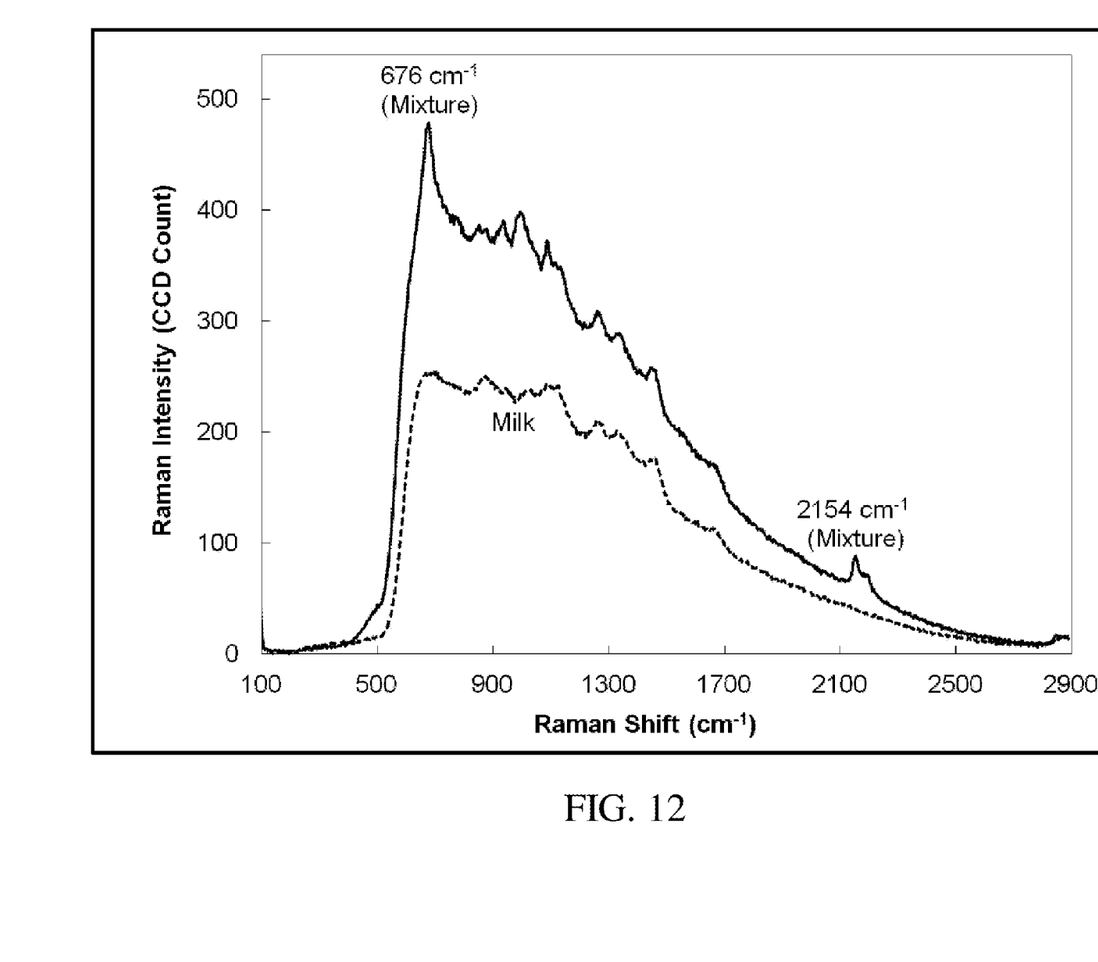
FIG. 12 is Raman spectra of milk and milk mixed with melamine and dicyandiamide.

FIGS. 11 and 12 show representative Raman spectra of the four powder samples in the wavenumber range of 100-2889 $cm^{-1}$. The spectra of the pure melamine and pure dicyandiamide (FIG. 11) share a relatively flat baseline. Raman peaks of the two chemicals were observed at different Raman shift positions, which formed the basis for detecting and distinguishing the adulterants in the milk powder. The highest peaks for melamine and dicyandiamide were found at 676 and 2154 $cm^{-1}$, respectively. Unlike the two pure chemicals, the two samples involving the milk powder exhibit a fluorescence background (FIG. 12), owing to the interaction of the 785-nm line-scan laser and the milk powder.

Several small Raman peaks attributed to lactose, proteins, and other constituents in the milk powder were found on the spectra of the two samples. The two highest peaks of melamine and dicyandiamide were observed on the spectrum of the milk-adulterant mixture, indicating the presence of the two adulterants in the milk powder. The Raman peaks of the two adulterants did not show on the spectrum of the pure milk powder.

Figure 13:
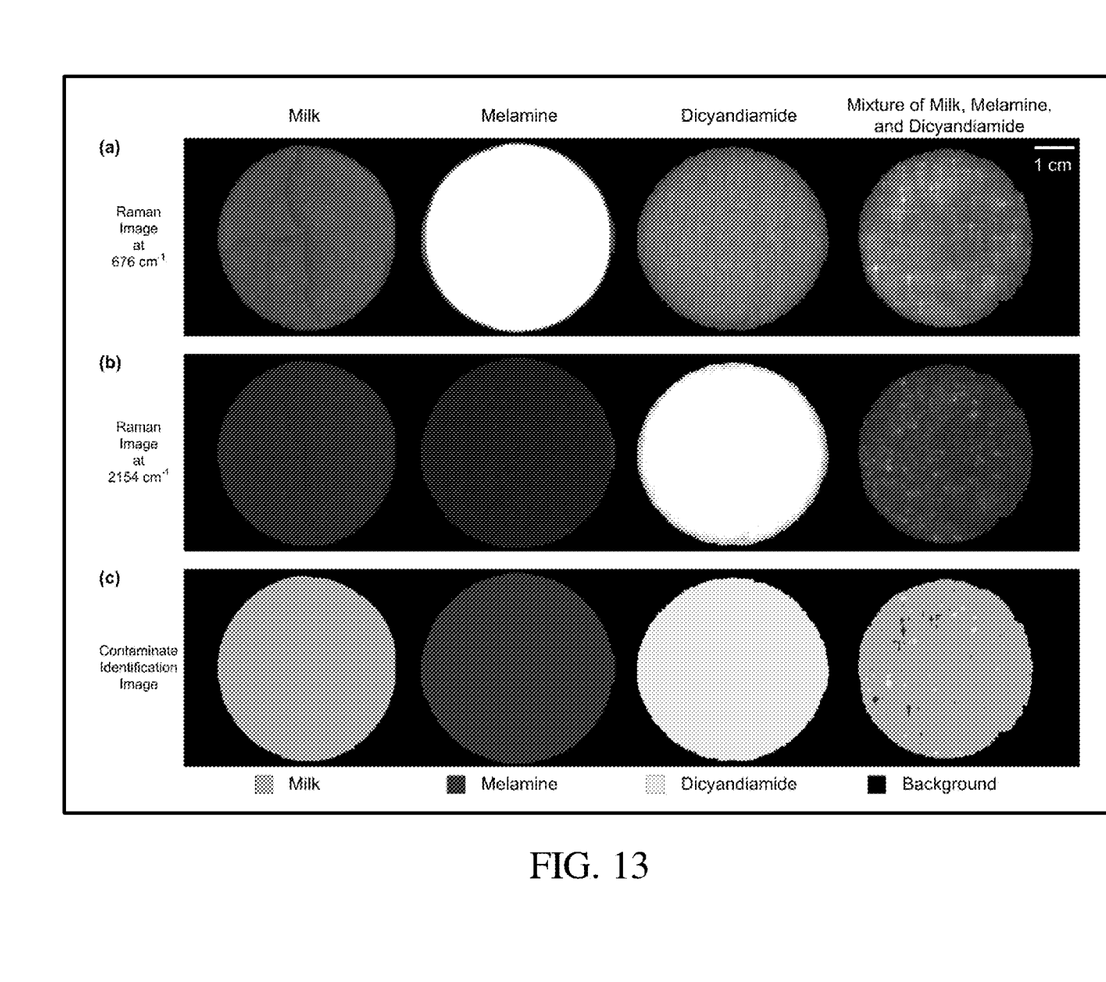
FIG. 13 is Raman images of milk, melamine, dicyandiamide, and milk-adulterant mixture.

Raman images of the four tested samples at the two highest peaks of melamine and dicyandiamide (i.e., 676 and 2154 $cm^{-1}$) are shown in FIG. 13 in the sections labeled (a) and (b), respectively. All the images were masked to remove the background. The images at the two peak positions exhibit different brightness patterns due to the wavenumber-dependent Raman intensities. Among the four samples, the images of pure melamine and dicyandiamide are the brightest at 676 and 2154 $cm^{-1}$, respectively.

The pixel intensities of the three pure samples show relatively consistent patterns in the petri dishes, while the images of the mixed sample show some bright pixel areas in the dark background due to the high Raman intensities of the adulterant particles in the milk powder. An image classification method for detecting multiple adulterants in the milk powder was previously developed by the inventors based on fluorescence correction and simple thresholding for single-band images at unique Raman peaks of the adulterants. The method was applied to the two images shown in FIG. 13 in the sections labeled (a) and (b), and the final Contaminate Identification Image shown in FIG. 13 section (c).

Melamine and dicyandiamide pixels were identified for the pure and mixed samples. The Contaminate Identification Image provides a clear view for the identification, spatial distribution, and some morphological features (e.g., particle size) for the two adulterants mixed in the milk powder. Such information is useful for most food safety and quality applications.

For the foregoing reasons, it is clear that the method and apparatus described herein provides an innovative method of detecting contamination in particulate substances. The current system may be modified in multiple ways and applied in various technological applications. The disclosed method and apparatus may be modified and customized as required by a specific operation or application, and the individual components may be modified and defined, as required, to achieve the desired result.

Although the materials of construction are not described, they may include a variety of compositions consistent with the function described herein. Such variations are not to be regarded as a departure from the spirit and scope of this disclosure, and all such modifications as would be obvious to one skilled in the art are intended to be included within the scope of the following claims.

What is claimed is:

1. A method for determining a composition of a sample, the method comprising the steps of:
    (a) providing a laser-emitting device that emits a continuous wave non-pulsed line-laser beam;
    (b) directing the line-laser beam to a beamsplitter;
    (c) positioning the beamsplitter to direct the line-laser beam onto a sample;
    (d) positioning the sample so that, as the line-laser beam traverses the sample, a light signal is emitted from sample;
    (e) providing a Raman spectrograph to receive the light signal and disperse the light signal to generate spectral data, a long-pass filter being attached adjacent to the spectrograph;
    (f) connecting a camera to the Raman spectrograph so that the camera receives the spectral data and forms a spectrum for each pixel of a line-laser image; and
    (g) transmitting the spectrum for each pixel of the line-laser image from the camera to a computer processor so that the processor receives the spectrum for each pixel of the line-laser image and determines a composition of the sample based on Raman imaging.

2. The method of claim 1 wherein, in step (a), the line-laser beam emits about a 785 nm laser.

3. The method of claim 1 wherein, in step (a), the line-laser laser beam is generated by an oscillating mirror oscillating at 100-300 Hz.

4. The method of claim 1 wherein, in step (b), the beamsplitter comprises a dichroic beamsplitter that deflects light wavelengths of about 785 nm and allows longer light wavelengths to pass unaltered.

5. The method of claim 1 wherein, in step (b), the beamsplitter deflects the line laser beam about 45 degrees relative to a face of the beamsplitter.

6. The method of claim 1 wherein, in step (c), the sample comprises an essentially dry particulate matter.

7. The method of claim 1 wherein, in step (c), the sample comprises a powder.

8. The method of claim 1 wherein, in step (c), the sample is positioned in a sample retention reservoir on a top portion of a positioning table.

9. The method of claim 1 wherein, in step (c), the sample is positioned in a sample retention reservoir on a top portion of a programmable one-axis motorized positioning table so that the positioning table is controlled by the processor described in step (g) via a stepping motor, the processor being in communication with the camera described in step (f).

10. The method of claim 1 wherein, in step (d), the light signal comprises a Raman shifted light signal.

11. The method of claim 1 wherein, in step (e), the spectrograph comprises an input slit aligned in a same vertical plane as an excitation line defined by the line-laser beam.

12. The method of claim 1 wherein, in step (e), the spectrograph comprises a prism-grating-prism component.

13. The method of claim 1 wherein in step (e), the spectrograph creates a two dimensional image, a first dimension comprising a spatial dimension and a second dimension comprising a spectral dimension.

14. The method of claim 1 wherein, in step (e), the spectrograph comprises an imaging spectrograph covering a wavelength range of 770-980 nm or a Raman shift range of −248.2-2534.8 $cm^{-1}$ with a spectral resolution of 0.3 nm or a Raman resolution of ~10 $cm^{-1}$.

15. The method of claim 1 wherein, in step (e), the long-pass filter is positioned inside the spectrograph to block light at and below a filter wavelength threshold.

16. The method of claim 1 wherein, in step (e), the long-pass filter is fixed in a filter holder inside a front C-mount of the spectrograph to block light at and below a filter wavelength threshold of 785 nm.

17. The method of claim 1 wherein, in step (e), a manual iris C-mount lens is attached to the imaging spectrograph.

18. The method of claim 1 wherein, in step (f), the camera comprises a charged coupled device (CCD) camera.

19. The method of claim 1 wherein, in step (f), the camera is fixed on a ball and socket mounting stage that is mounted on top of a manual translation stage so that a user can adjust a position of the camera and the spectrograph.

20. The method of claim 1 wherein, in step (g), the processor receives the spectrum for each pixel of the line-laser image, the spectrum comprising a Raman spectrum; a material associated with each pixel of the line-laser image being identified based on a comparison of the Raman spectrum for each pixel, relative to a reference Raman spectrum; a composition of the sample material being characterized by a collective analysis of all of the pixels for the line-laser image.

21. The method of claim 1 wherein, in step (g), the line-scan image comprises a Raman image, and the processor further assigns a color, shade, and intensity to each pixel to provide a visualization of the sample composition.

22. The method of claim 21 wherein the visualization comprises a contaminate identification image.

23. An apparatus for determining a composition of a sample, the apparatus comprising:

a laser-emitting device emitting a continuous wave non-pulsed line-laser beam;

a beamsplitter positioned to deflect the line-laser beam;

a sample retention reservoir retaining a sample, the line laser beam traversing the sample, the sample emitting a light signal in response to the line-laser beam;

a Raman spectrograph receiving the light signal, and dispersing the light signal to generate spectral data, a long-pass filter being attached adjacent to the spectrograph;

a camera receiving the spectral data, and forming a spectrum for each pixel of a line-laser image; and a processor receiving the spectrum for each pixel of the line-laser image, and determining a composition of the sample based on Raman imaging.

24. The apparatus of claim 23 wherein the line-laser beam is generated by an oscillating mirror within the laser-emitting device, the mirror oscillating at 100-300 Hz.

25. The apparatus of claim 23 wherein the line-laser beam is about 785 nm.

26. The apparatus of claim 23 wherein the beamsplitter is structured so that the light signal passes through the beamsplitter.

27. The apparatus of claim 23 wherein the beamsplitter comprises a dichroic beamsplitter that allows light wavelengths greater than about 785 nm to pass through unaltered.

28. The apparatus of claim 23 wherein the apparatus is structured so that the light signal is a Raman shifted light signal.

29. The apparatus of claim 23 wherein the sample is positioned in the sample retention reservoir on a top portion of a programmable one-axis motorized positioning table so that the positioning table is controlled by the processor via a stepping motor, the processor interface being structured so that the processor is in communication with the camera.

30. The apparatus of claim 23 wherein the spectrograph is structured so that the light signal enters the spectrograph through a slit in the imaging spectrograph.

31. The apparatus of claim 23 wherein the apparatus is structured so that the spectrograph comprises an input slit aligned in a same vertical plane as an excitation line defined by the line-laser beam.

32. The apparatus of claim 23 wherein the spectrograph comprises a prism-grating-prism component.

33. The apparatus of claim 23 wherein the spectrograph comprises an imaging spectrograph covering a wavelength range of 770-980 nm or a Raman shift range of −248.2-2534.8 $cm^{-1}$ with a spectral resolution of 0.3 nm or a Raman resolution of ~10 $cm^{-1}$.

34. The apparatus of claim 23 wherein the long-pass filter is positioned inside the spectrograph to block light at and below a filter wavelength threshold.

35. The apparatus of claim 23 wherein the long-pass filter is fixed in a filter holder inside a front C-mount of the spectrograph to block light at and below a filter wavelength threshold of 785 nm.

36. The apparatus of claim 23 wherein a manual iris C-mount lens is attached to the imaging spectrograph.

37. The apparatus of claim 23 wherein the camera comprises a charged coupled device (CCD) camera.

* * * * *